(12) United States Patent
Nishi et al.

(10) Patent No.: US 9,713,527 B2
(45) Date of Patent: Jul. 25, 2017

(54) MULTILENS INTRAOCULAR LENS SYSTEM WITH INJECTABLE ACCOMMODATION MATERIAL

(75) Inventors: Okihiro Nishi, Osaka (JP); Kayo Nishi, Osaka (JP); Shiao H. Chang, Pasadena, CA (US); Jerry Kaeni, Upland, CA (US)

(73) Assignee: RxSight, Inc., Aliso Viejo, CA (US)

( * ) Notice: Subject to any disclaimer, the term of this patent is extended or adjusted under 35 U.S.C. 154(b) by 1112 days.

(21) Appl. No.: 11/489,847

(22) Filed: Jul. 20, 2006

(65) Prior Publication Data

US 2006/0271186 A1    Nov. 30, 2006

Related U.S. Application Data

(63) Continuation-in-part of application No. 11/118,253, filed on Apr. 29, 2005, now abandoned.

(Continued)

(51) Int. Cl.
*A61F 2/16* (2006.01)
*A61L 27/18* (2006.01)
(Continued)

(52) U.S. Cl.
CPC .......... *A61F 2/1648* (2013.01); *A61F 2/1613* (2013.01); *A61F 2/1627* (2013.01);
(Continued)

(58) Field of Classification Search
CPC ......... A61F 2002/1651; A61F 2/1613–2/1659; A61F 2250/0008–2250/001;
(Continued)

(56) References Cited

U.S. PATENT DOCUMENTS

| 4,253,199 A | 3/1981 | Banko |
| 4,254,509 A | 3/1981 | Tennant |

(Continued)

FOREIGN PATENT DOCUMENTS

| EP | 0335312 | 4/1989 |
| WO | WO-93/25187 | 12/1993 |

(Continued)

OTHER PUBLICATIONS

Rochester.edu article entitled "Chem 421: Introduction of Polymer Chemistry Polymer Properties and MW" located on line at http://chem.chem.rochester.edu/~chem421/propsmw.htm.*

(Continued)

*Primary Examiner* — Paul Prebilic

(57) ABSTRACT

The invention relates to a multi-lens intraocular lens system having an accommodation material between the lenses. The system comprises an posterior lens attached to the posterior surface of the capsular bag and an anterior lens attached to the anterior surface of the capsular bag. The anterior and posterior lenses have different optical properties providing different degrees and types of correction. An accommodation material is place between the anterior and posterior lenses. The accommodation material may comprise of one or more macromers, which, when polymerized, adjust the properties of the accommodation material.

16 Claims, 14 Drawing Sheets

Related U.S. Application Data

(60) Provisional application No. 60/567,331, filed on Apr. 30, 2004, provisional application No. 60/782,176, filed on Mar. 14, 2006.

(51) Int. Cl.
   *A61F 9/00* (2006.01)
   *A61L 27/50* (2006.01)
   *A61F 2/30* (2006.01)

(52) U.S. Cl.
   CPC .......... *A61F 2/1635* (2013.01); *A61F 9/0017* (2013.01); *A61L 27/18* (2013.01); *A61L 27/50* (2013.01); *A61F 2002/1699* (2015.04); *A61F 2002/30581* (2013.01); *A61F 2002/30583* (2013.01); *A61F 2210/0085* (2013.01); *A61L 2430/16* (2013.01)

(58) Field of Classification Search
   CPC ...... A61F 2250/0012; A61F 2250/0053; A61F 2250/0065; A61F 2250/0091
   USPC .......... 623/6.11, 6.13, 6.14, 6.34, 6.37, 6.56
   See application file for complete search history.

(56) References Cited

U.S. PATENT DOCUMENTS

| | | | |
|---|---|---|---|
| 4,608,650 A | 8/1986 | Kapadia | |
| 4,685,922 A | 8/1987 | Peyman | |
| 4,693,717 A * | 9/1987 | Michelson | 623/6.13 |
| 4,790,847 A | 12/1988 | Woods | |
| 4,842,601 A | 6/1989 | Smith | |
| 4,872,877 A | 10/1989 | Tiffany | |
| 4,892,543 A | 1/1990 | Turley | |
| 4,932,966 A | 6/1990 | Christie et al. | |
| 4,969,912 A | 11/1990 | Kelman et al. | |
| 5,201,762 A * | 4/1993 | Hauber | 623/6.34 |
| 5,213,579 A | 5/1993 | Yamada et al. | |
| 5,275,623 A | 1/1994 | Sarfarazi | |
| 5,391,590 A * | 2/1995 | Gerace et al. | 523/107 |
| 5,411,553 A | 5/1995 | Gerace et al. | |
| 5,476,512 A * | 12/1995 | Sarfarazi | A61F 2/16 623/6.39 |
| 5,476,515 A | 12/1995 | Kelman et al. | |
| 5,607,472 A | 3/1997 | Thompson | |
| 5,702,411 A | 12/1997 | Back et al. | |
| 6,066,172 A * | 5/2000 | Huo et al. | 623/6.56 |
| 6,231,603 B1 * | 5/2001 | Lang | A61F 2/1613 623/6.24 |
| 6,413,262 B2 * | 7/2002 | Saishin et al. | 606/107 |
| 6,450,642 B1 * | 9/2002 | Jethmalani et al. | 351/219 |
| 6,464,725 B2 * | 10/2002 | Skotton | 623/6.34 |
| 6,599,317 B1 * | 7/2003 | Weinschenk et al. | 623/6.34 |
| 6,638,305 B2 * | 10/2003 | Laguette | 623/6.37 |
| 6,747,090 B2 * | 6/2004 | De Groot et al. | 524/555 |
| 7,156,101 B2 | 1/2007 | Terwee et al. | |
| 7,438,723 B2 * | 10/2008 | Esch | 623/6.13 |
| 7,559,949 B2 * | 7/2009 | Pinchuk | 623/6.56 |
| 8,162,927 B2 * | 4/2012 | Peyman | A61F 2/16 128/898 |
| 2002/0016629 A1 * | 2/2002 | Sandstedt | A61B 3/1015 623/6.11 |
| 2002/0111678 A1 * | 8/2002 | Zadno-Azizi et al. | 623/6.34 |
| 2002/0165522 A1 | 11/2002 | Holmen | |
| 2002/0169505 A1 | 11/2002 | Jethmalani et al. | |
| 2003/0004569 A1 * | 1/2003 | Haefliger | A61F 2/1627 623/6.34 |
| 2003/0060878 A1 * | 3/2003 | Shadduck | A61F 2/1613 623/6.13 |
| 2003/0088044 A1 | 5/2003 | Hodd et al. | |
| 2004/0082995 A1 * | 4/2004 | Woods | 623/6.34 |
| 2005/0246018 A1 | 11/2005 | Grubbs et al. | |
| 2006/0271186 A1 * | 11/2006 | Nishi et al. | 623/6.13 |
| 2007/0118216 A1 * | 5/2007 | Pynson | 623/6.34 |
| 2007/0129802 A1 * | 6/2007 | Jethmalani | A61F 2/16 623/6.22 |
| 2008/0086207 A1 * | 4/2008 | Sandstedt | A61F 2/16 351/159.4 |
| 2008/0300680 A1 * | 12/2008 | Joshua | 623/6.37 |
| 2012/0290084 A1 * | 11/2012 | Coroneo | 623/6.13 |

FOREIGN PATENT DOCUMENTS

| | | |
|---|---|---|
| WO | WO00/41650 | 7/2000 |
| WO | WO-2000/061036 | 10/2000 |

OTHER PUBLICATIONS

Nishi, Okihiro, et al.; Accommodation Amplitude After Lens Refilling With Injectable Silicone by Sealing the Capsule With a Plug in Primates; arch Ophthalmol. 1998; 116:1358-1361.

Nishi, Okihiro, et al.; Capsule opacification after refilling the capsule with an inflatable endocapsular balloon; J Cataract Refract Surg. 23:1548-1555, Dec. 1997.

Nishi, Okihiro, et al.; Controlling the Capsular Shape in Lens Refilling; Arch Ophthalmol. 1997; 115:507-510.

Nishi, Okihiro, et al.; Lens refilling with injectable silicone in rabbit eyes; J Cataract Refract Surg. 24:975-982, Jul. 1998.

International Search Report issued Dec. 7, 2007 (published Mar. 20, 2008), during the prosecution of International Application No. PCT/US07/63846.

Written Opinion issued Dec. 7, 2007 (published Sep. 14, 2008), during the prosecution of International Application No. PCT/US07/63846.

International Preliminary Report on Patentability issued Sep. 16, 2008 (published Sep. 16, 2008), during the prosecution of International Application No. PCT/US07/63846.

Heys et al., "Massive increase in the stiffness of the human lens nucleus with age: the basis for presbyopia?", Mol. Vis., 10: 956-963 (Dec. 2004), (abstract only).

* cited by examiner

MULTILENS INTRAOCULAR LENS SYSTEM WITH INJECTABLE ACCOMMODATION MATERIAL

CROSS-REFERENCE TO RELATED APPLICATIONS

This application claims priority to U.S. Provisional Application No. 60/782,176 which was filed on Mar. 14, 2006 and is a continuation-in-part of U.S. Ser. No. 11/118,253, filed on Apr. 29, 2005.

STATEMENT REGARDING FEDERALLY SPONSORED RESEARCH OR DEVELOPMENT

Not applicable.

REFERENCE TO A COMPACT DISK APPENDIX

Not applicable.

TECHNICAL FIELD

The invention relates to a novel intraocular lens system having a pair of lenses implanted in the capsular bag of a patient. The lenses have different optical properties. The space between the first and second lenses is filled with a material which aids in the accommodation capability of the lens system. The first lens is implanted behind the capsulorhexis opening to provide the refractive power of the eye and seal the capsulorhexis. The second lens is implanted next to the posterior surface of the bag to prevent the PCO. The accommodation material has a refractive index similar to that of the aqueous humor thereby reducing any potential interference with the lenses.

BACKGROUND OF THE INVENTION

Cataract extraction is the most common ophthalmic surgical procedure performed in the United States. Extracapsular cataract extraction involves cutting a portion of the anterior capsule (anterior capsulorhexis) followed by removal of the nucleus. Alternatively, a probe may be inserted through the anterior capsule and ultrasonically vibrated, transforming lens material into an emulsion, which is then irrigated and aspirated from the capsular bag (phacoemulsification). After removal of the natural lens, images no longer focus on the retina and a replacement lens must be provided for clear vision. Replacement lenses can be glasses, contact lenses or intraocular lenses. Of these, intraocular lenses give the greatest convenience and undistorted vision, however, lack the ability of a natural lens to accommodatively focus on near and far objects.

When a person looks at an object, light is reflected from the object through the cornea, the aqueous humor, through the pupil and into the lens which converges the light through the vitreous body onto the retina. To clearly focus on near objects, light rays must bend more. To accomplish this, the lens becomes more curved and thicker. Most of this change comes from pulling and relaxing the capsular bag at its equator. The equator of the bag is attached to the ciliary muscle by filaments called the zonules which are in turn attached to the ciliary muscle. When looking at a near object, the ciliary muscle tenses and contracts moving the muscle slightly inward and relaxing the pull on the zonules, allowing the capsular bag to become more curved and thickened from front to back. The lens itself is composed of interlocking fibers which affect the elastic movement of the lens so that as the lens changes shape the fibers alter their curvature. As a person ages, the accommodative ability of the lens decreases due to changes in the eye. Age related eye changes include thickening and hardening of the lens, an increase in the amount of insoluble protein in the lens, a migration in the points of attachment of the zonules away from the equator of the capsule, and partial liquefaction of the vitreous body.

Several attempts have been made to provide the eye with focal length accommodation. The most familiar of these are bi or multi-focal lenses. These are used in glasses, contacts, and intraocular lenses but have a disadvantage in that the focal accommodation is dependent upon direction of focus. These lenses do not provide true accommodation. The accommodating implant provides vision over a continuous range of distance by affecting a change in the vergence power of the eye resulting from the implant design that changes eye optical power or implant position in response to a stimulus.

U.S. Pat. No. 4,254,509 discloses a lens which takes advantage of the ciliary muscle. However, this lens is placed in the anterior chamber of the eye. Such implants are at times accompanied by complications such as damage to the vascular iris.

U.S. Pat. No. 4,253,199 discloses a lens attached directly to the ciliary body. The lens is in a more natural position but requires suturing to the ciliary body risking massive rupture during surgery and bleeding from the sutures.

U.S. Pat. No. 4,685,922, incorporated herein by reference, discloses a chambered lens system for which the refractive power can be changed. Such alteration is permanent, accomplished by rupture of the chambers.

U.S. Pat. No. 4,790,847 provides a single lens for in capsular bag implantation using rearwardly biased haptics which engage the capsular bag at its equator and move the lens forward and backward upon contraction and relaxation of the ciliary muscles.

U.S. Pat. No. 4,842,601, incorporated herein by reference, discloses a two section deformable lens assembly for implanting in the capsular bag. The lens allows division of refractive power and takes advantage of the action of the ciliary body and zonules on the capsular bag. This lens system is assembled after insertion.

U.S. Pat. No. 4,892,543, discloses another two lens assembly for placement in the posterior chamber, possibly in the bag where the capsular bag is not removed. This lens allows dividing the refractive power between two lenses and introduces a variable focal length in one of the lenses by compressing a flexible wall of one lens against the convex surface of the second fixed lens. This requires that the first and second lens be in substantially adjacent positions.

U.S. Pat. No. 4,932,966, incorporated herein by reference, presents an accommodative lens in which two lenses joined at their periphery enclosed a fluid filled sack, accommodation being accomplished selectively changing the fluid pressure in the sac. One lens is a rigid base lens and the other lens is membrane-like, the equatorial diameter of the lens assembly being substantially that of a dilated pupil and is supported by bladders or haptics.

U.S. Pat. No. 5,275,623 discloses dual and thick lens optics capable of accommodating focus at a range of distances in a unitary structure. It uses the eye capsule's natural shaping from the ciliary body to accommodate the focus.

PCT Application No. WO 00/61036 discloses an open chamber, elliptical, accommodating lens system. It uses a pair of lenses attached to each other by two or more haptics.

The system uses the eye capsule's natural shaping from the ciliary body to accommodate the focus of the lenses.

Published United States Patent Application No. 2005/0246018 discloses the use of an injectable accommodation material where the lens is either embedded in the material or is placed in the anterior capsule. While this system is effective in providing accommodation, posterior capsular opacification is sometimes encountered with this system. Thus, there continues to exist a need for an improved accommodation system which overcomes the problems of the prior art.

BRIEF SUMMARY OF THE INVENTION

The present invention comprises an intraocular lens system comprising a pair of lenses placed within the capsular bag and an accommodation material injected between the lenses. One lens is placed at the anterior portion of the capsular bag (anterior lens) and the other at the posterior surface of the capsular bag (posterior lens). The accommodation material may have a refractive index approximately the same as the aqueous humor and has sufficient elasticity to expand and contract when acted upon by the zonules. The accommodation material is capable of being injected into the capsular bag, yet is capable of supporting the anterior lens. In one embodiment, the anterior lens provides a seal for the injectable accommodation material as well as diopter power to the patient. The anterior lens power selected is preferably higher than the patient's emmotropia power to maximize the accommodation amplitude. In one embodiment, the posterior lens incorporates a squared edge to prevent posterior capsular opacification (PCO). In yet another embodiment, the posterior lens has a negative diopter power to provide the patient with an emmotropia vision when combined with the anterior lens.

In another embodiment, a posterior capsulorhexis is created and the posterior lens is implanted to seal the posterior opening. This procedure has also been found to prevent posterior capsular opacification.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

DETAILED DESCRIPTION OF THE INVENTION

Figure 1:
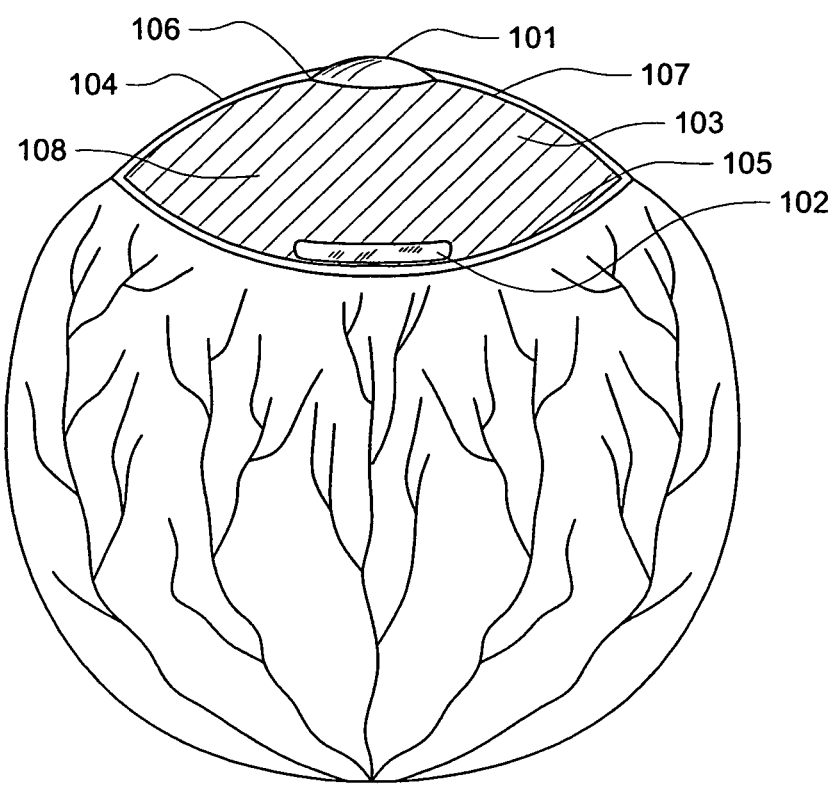
FIG. 1 is a cross section of an eye with the intraocular lens system of the invention in place.

Referring to FIG. 1, the natural lens of a patient is replace with an intraocular lens system comprising an anterior lens 101, a posterior lens 102 and an accommodation material 103. The posterior lens 102, is placed at the posterior surface 105 of the capsular bag 104 and the anterior lens 101 is placed anteriorly in the capsular bag 104 behind the capsular opening 106. The space between the lenses is filled with an accommodation material 103. The anterior and posterior lenses 101, 102 may have different optical properties and may provide different degrees and types of correction.

Figure 5:
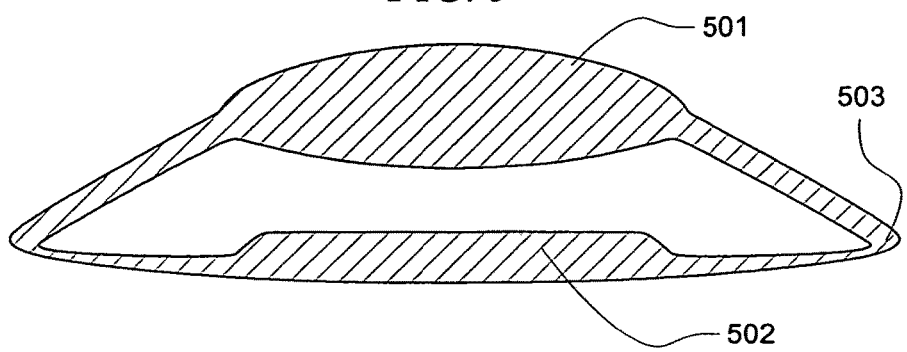
FIG. 5 is a cross section of the anterior and posterior lenses joined together.

In practice of the invention, the natural lens of the patient is removed using standard surgical procedures. Typically this is done by phaeco-emulsification. After removal of the natural lens, the posterior lens is introduced into the capsular bag first followed by the anterior lens. In one embodiment, shown in FIG. 5, the anterior 501 and posterior lenses 502 are joined or fused together at the outer edges of the lenses 503. Alternatively, the lenses may be separately anchored in the capsular bag. Anchoring may be done using standard techniques including the use of plate haptics or through the use of disk lenses. The anterior lens is placed such that it closes or seals the opening created during removal of the natural lens.

Figure 2:
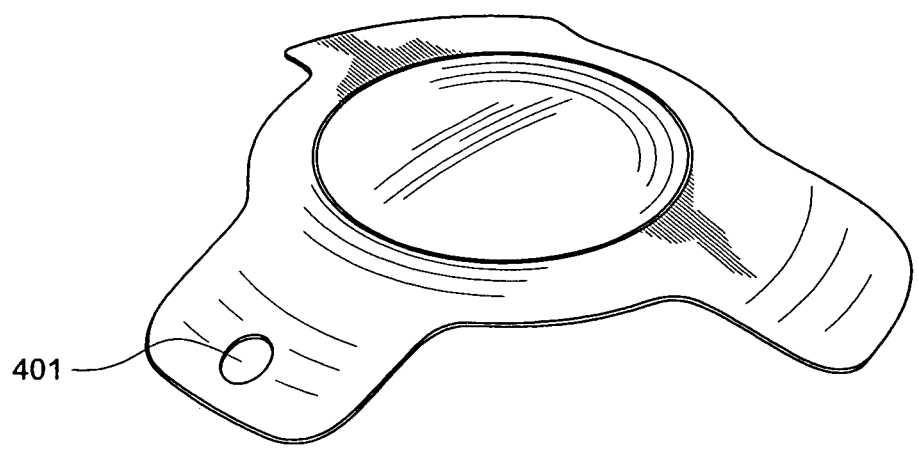
FIG. 2 is a perspective view of a tripod lens which is used in the practice of the invention.
Figure 3:
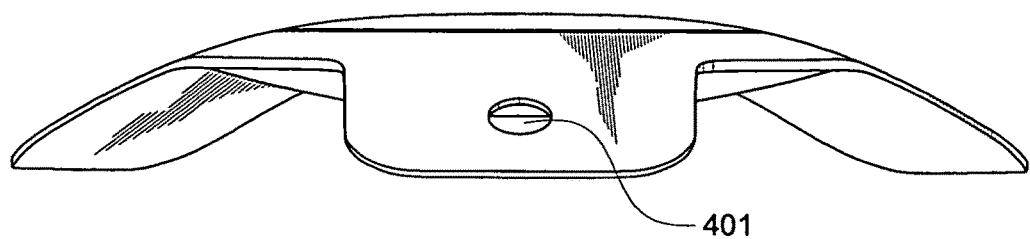
FIG. 3 is a side view of a tripod lens.
Figure 4:
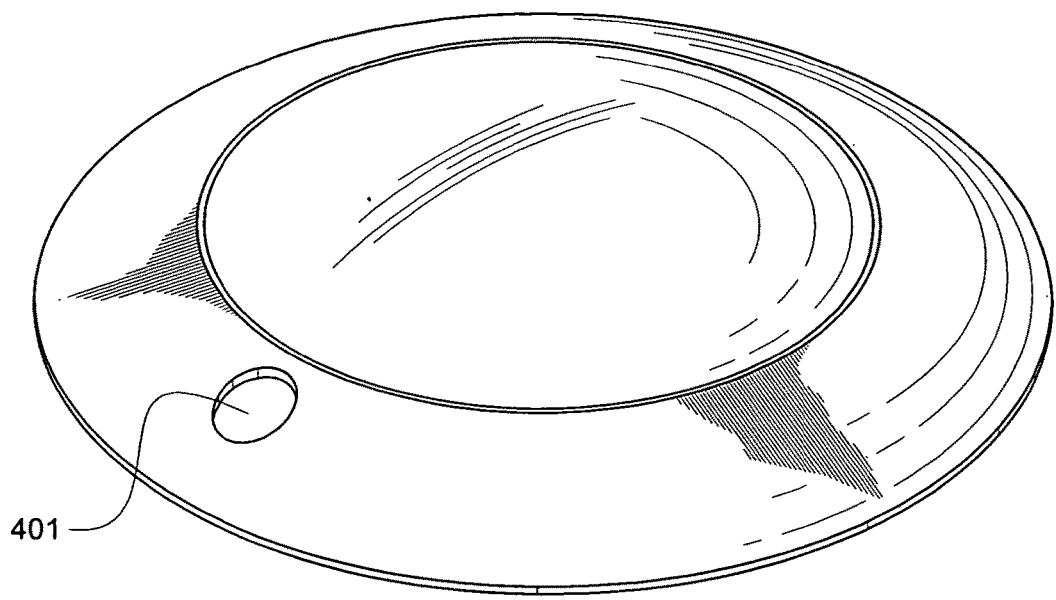
FIG. 4 is a plate lens which is used as the anterior lens of the invention.

The anterior lens generally comprises a soft material including, but not limited to silicone, soft acrylic or hydrogel so that the lens may be folded to aid in insertion. Any form of intraocular lens may be used to include adjustable lenses such as those described in U.S. Pat. No. 6,450,642. In one embodiment, the lens is biconvex with a relatively high diopter power. For example, in one embodiment, the lens will have a diopter power of +30. The use of a high diopter lens as the anterior lens is to maximize the accommodation amplitude during lens forward movement as a result of zonule contraction. In the case of a plate lens as shown in FIG. 4, a small hole or port 401, typically about 0.75 mm or less is provided in the plate region of the lens, typically about 1.0 mm from the edge. In the case of a lens with plate haptics such as those shown in FIGS. 2 and 3, the hole or port 401 may be located in one of the haptic legs. While FIGS. 2 and 3 show a tripod lens, the lens may have from 2 to 4 haptic arms to attach the lens. The hole or port 401, allows injection of the accommodation material after the lenses are in place. The lens is generally placed just behind the capsulorhexis thereby acting as a plug for refilling the capsular bag with the accommodation material.

Figure 6:
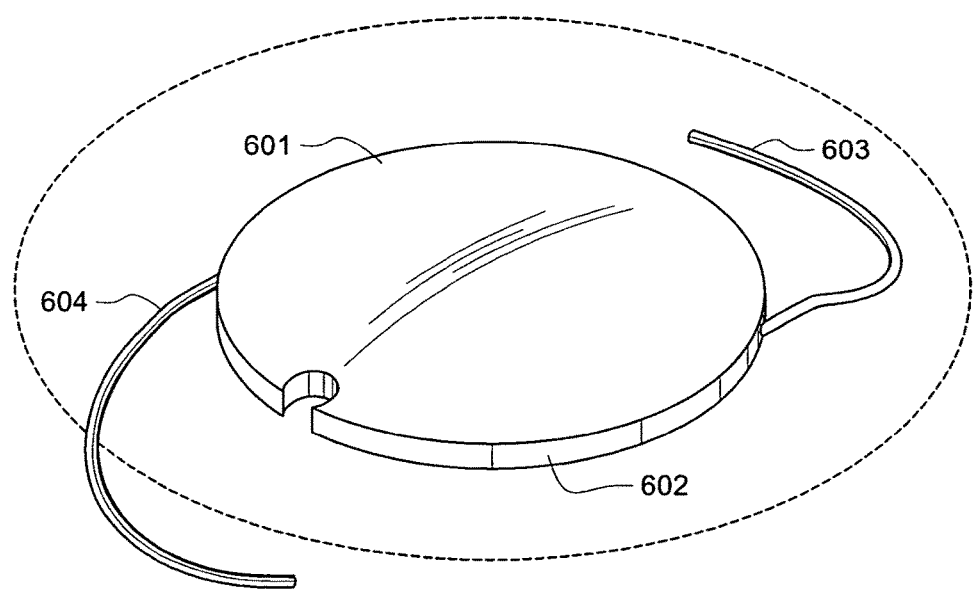
FIG. 6 is a perspective view of the posterior lens of the invention.
Figure 7:
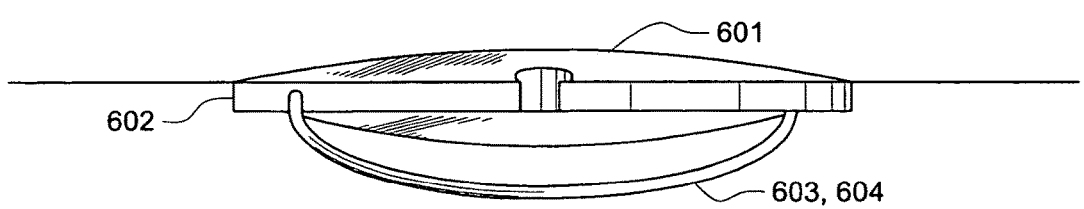
FIG. 7 is a side view of the posterior lens of the invention.

The posterior lens 102 shown in FIG. 1 may also comprises a flexible material including, but not limited to, silicone, soft acrylic or hydrogel, to allow the lens to be folded for insertion. In one embodiment, the lens has a negative power, for example –10 Diopter. As shown in FIGS. 6 and 7, the posterior lens 601 may have a squared edge 602. The use of a squared edge reduces the occurrence of posterior capsula opacification. As referenced in FIG. 1, the posterior lens 102 is placed next to the posterior surface 105 of the capsular bag 104. In this configuration, the posterior lens helps prevent PCO and provides emmotropic vision when combined with the anterior lens. In one embodiment, show in FIGS. 6 and 7, the posterior lens is held in place by use of haptics 603, 604.

As noted above, the anterior and posterior lenses should have different optical properties such that they each provide different degrees and types of correction. The two lenses, when in place, should compliment each other so as to provide emmotropic vision to the patient.

In one embodiment, the anterior lens 101 is placed within the capsular bag 104 such that it seals the capsular opening 106 created during the removal of the natural lens. When the anterior lens 101 is forced against the anterior wall 107 of the capsular bag 104, the lens closes and seals the capsular opening 106 and prevents the accommodation material 103 from leaking out of the capsular bag 104. The anterior lens 101 can be forced against the anterior wall by any means known in the art.

In one embodiment, the anterior lens is pushed forward by the haptics used to hold the anterior lens in place. In this embodiment, the haptic is attached to the anterior lens in such a way as to urge the lens forward, pressing the lens against the anterior wall. In this embodiment, the haptic should be flexible enough to allow for the forward movement of the anterior lens during accommodation.

In another embodiment, the anterior lens 101 is pushed against the anterior wall by the accommodation material 103. This is accomplished by filling the capsular bag 104 with sufficient accommodation material 103 such that it forces the anterior lens 101 against the anterior wall 106. The forcing of the anterior lens 101 against the anterior wall 106 can also be accomplished by employing an anterior lens which comprises a material having a lower specific gravity than the accommodation material. This gives the lens "buoyance" on the accommodation material 103 to force the lens against the anterior wall 106. In yet another embodiment, various combinations of these methods can be used.

Figure 8:
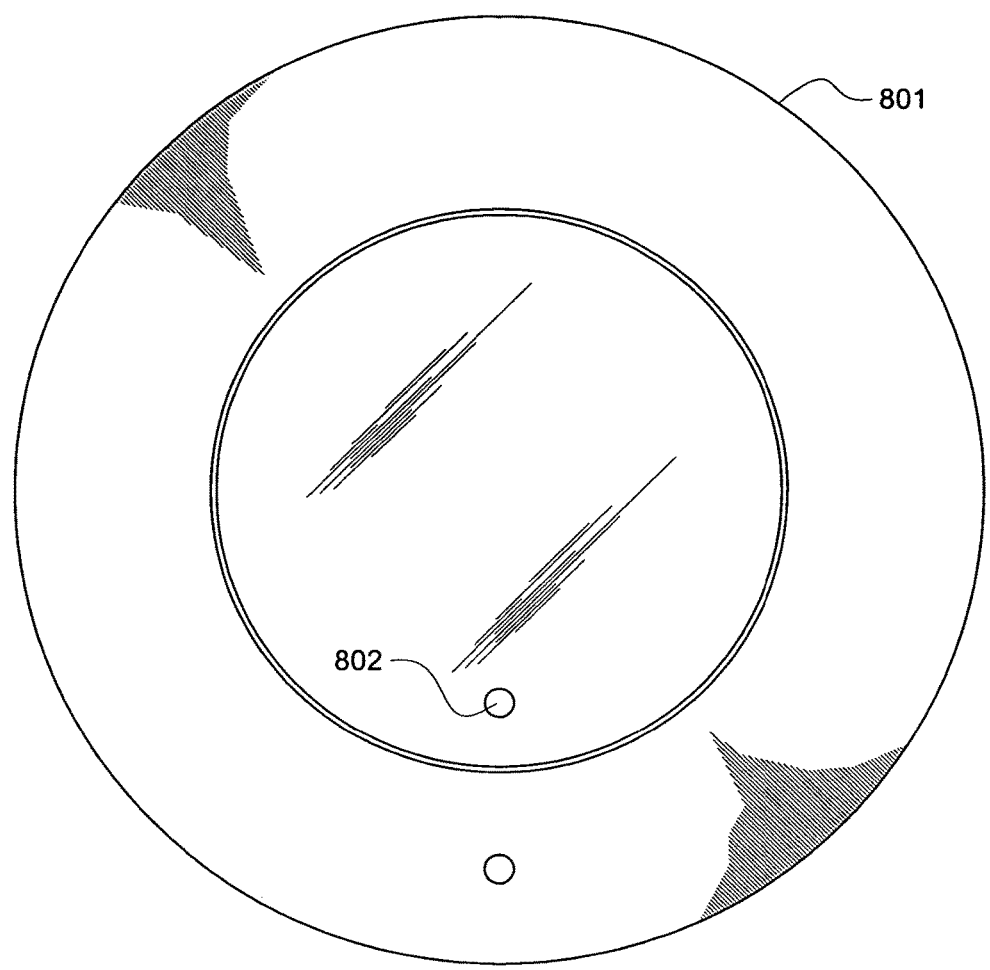
FIG. 8 is a plate lens which may be used for the anterior lens of the invention.
Figure 9:
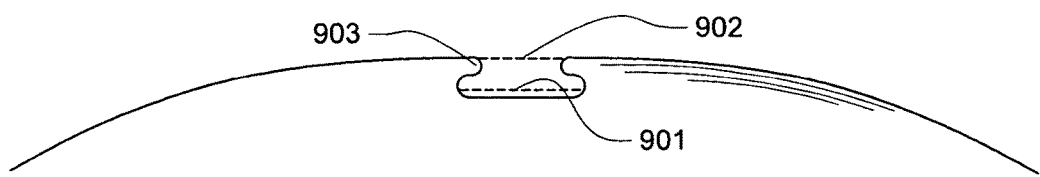
FIG. 9 is a cross section of an anterior lens showing one embodiment of a positioning cavity.
Figure 10:
FIG. 10 is a photograph of a rabbit eye 17 days after implantation system of the invention.
Figure 11:
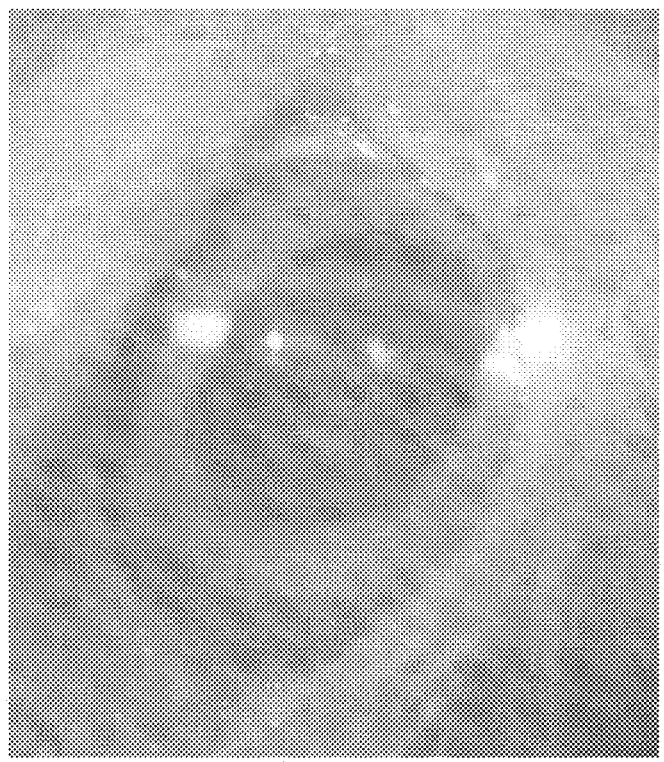
FIG. 11 is a photograph of another rabbit eye 17 days after implantation.
Figure 12:
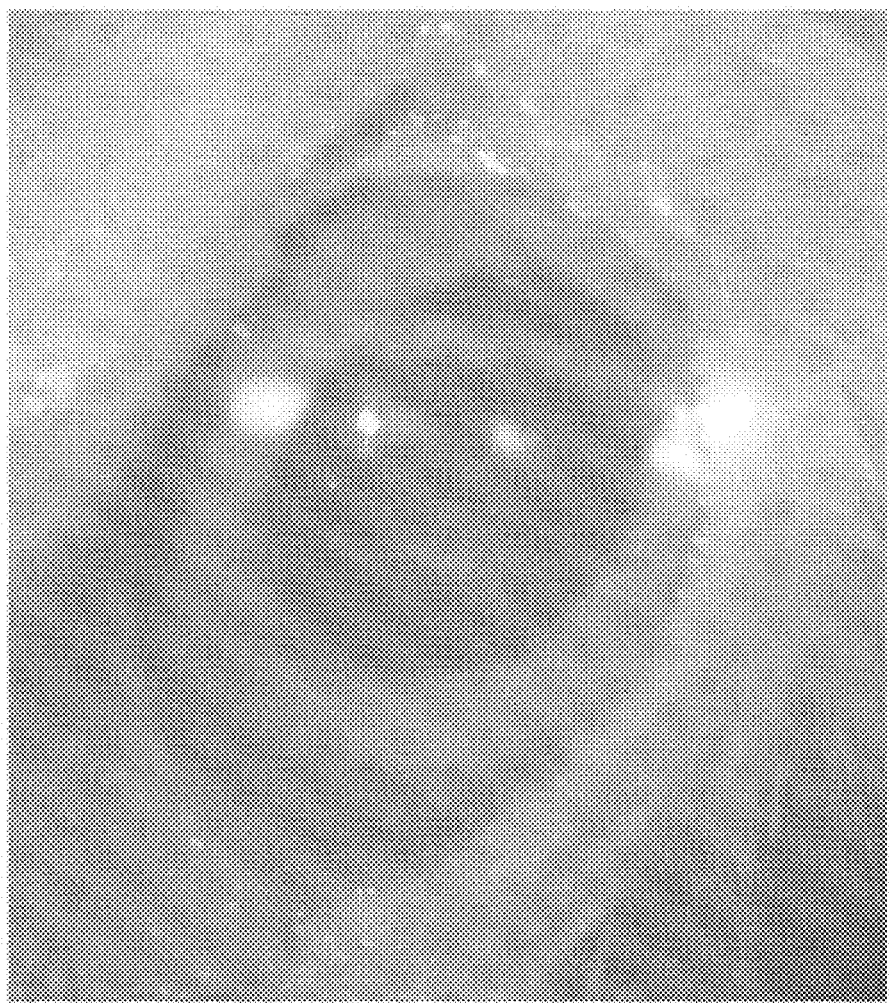
FIG. 12 is a third rabbit eye 17 days after implantation.
Figure 13:
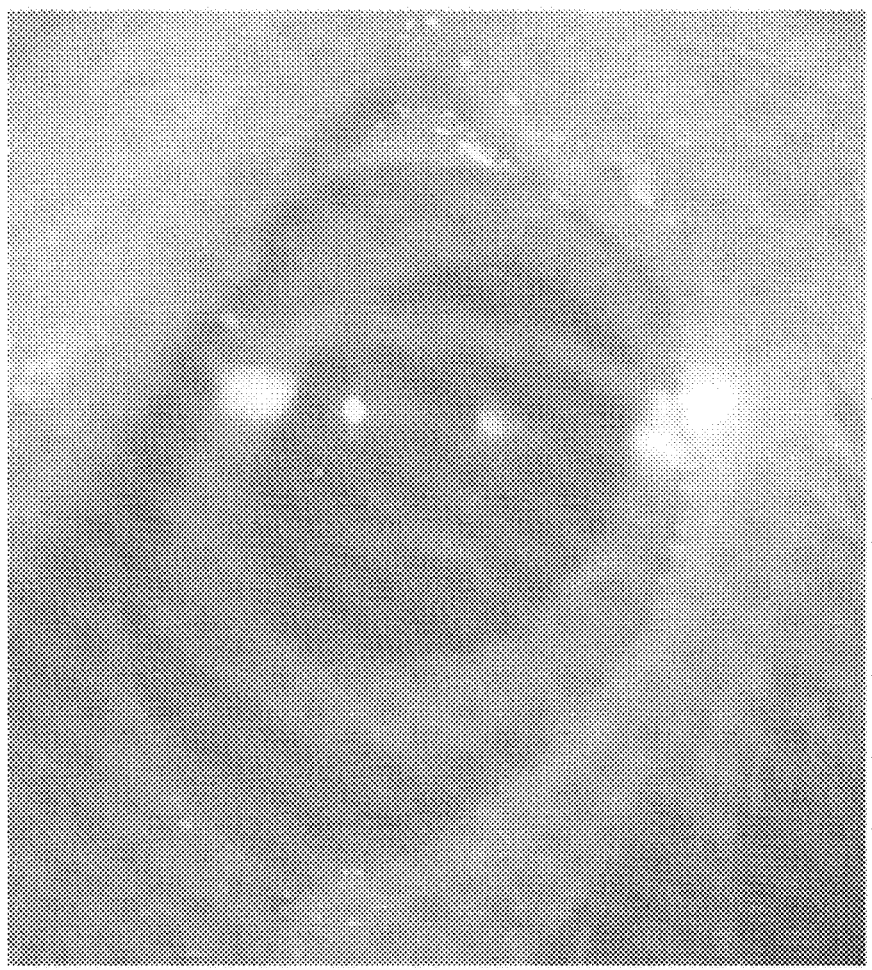
FIG. 13 is a fourth rabbit eye 17 days after implantation.
Figure 14:
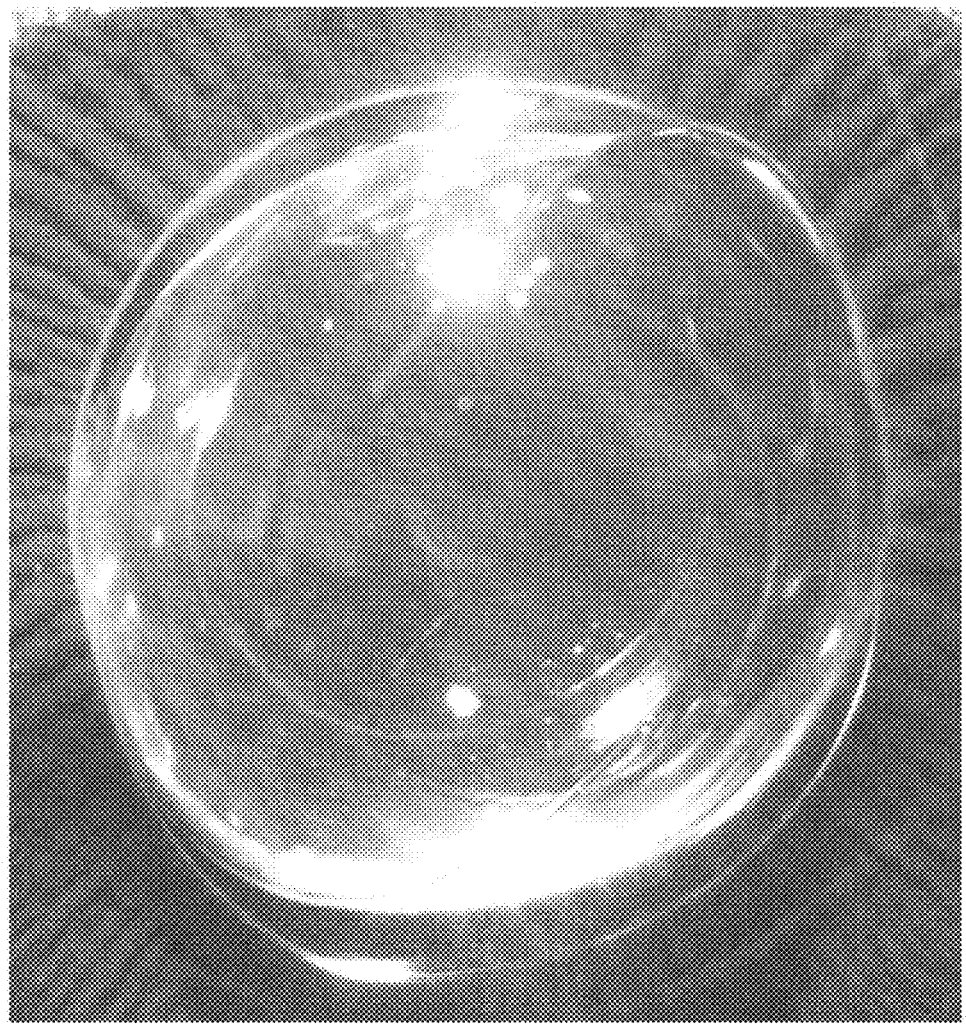
FIG. 14 is a posterior view of a pig cadaver eye with a dual lens system.
Figure 15:
FIG. 15 is a front view of a pig cadaver eye with a dual lens system.
Figure 16:
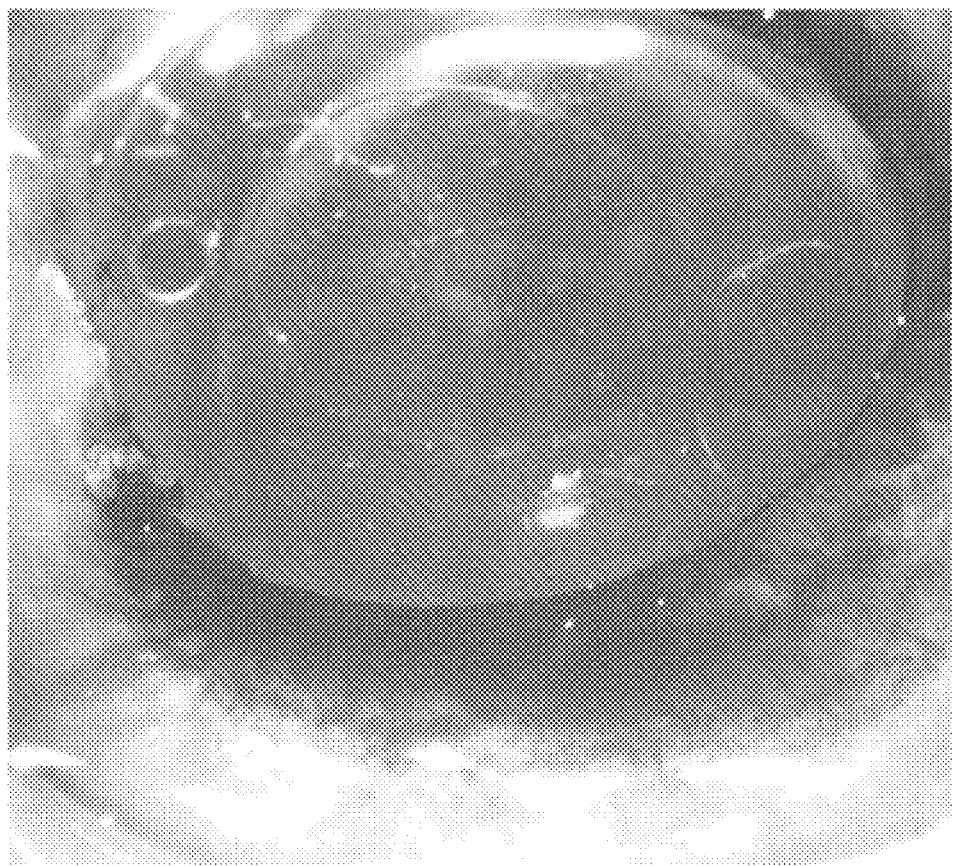
FIG. 16 is an anterior view of a second pig cadaver eye with a dual lens system.
Figure 17:
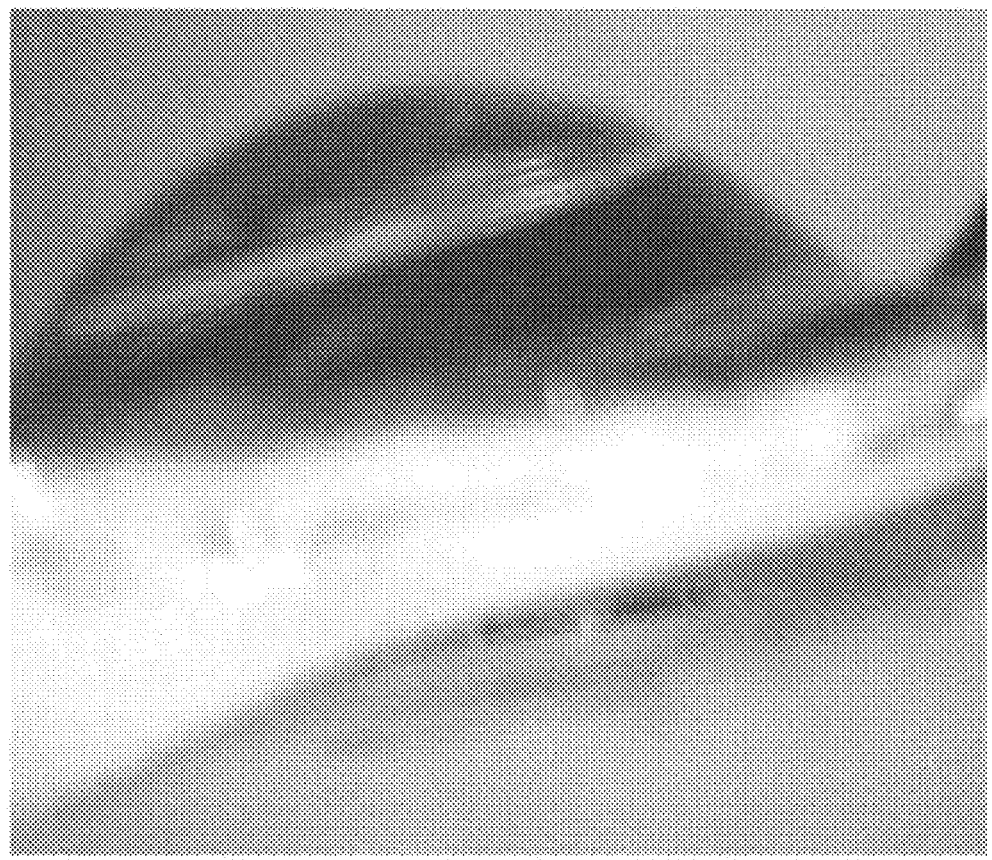
FIG. 17 is a side view of a pig cadaver eye with a dual lens system.
Figure 18:
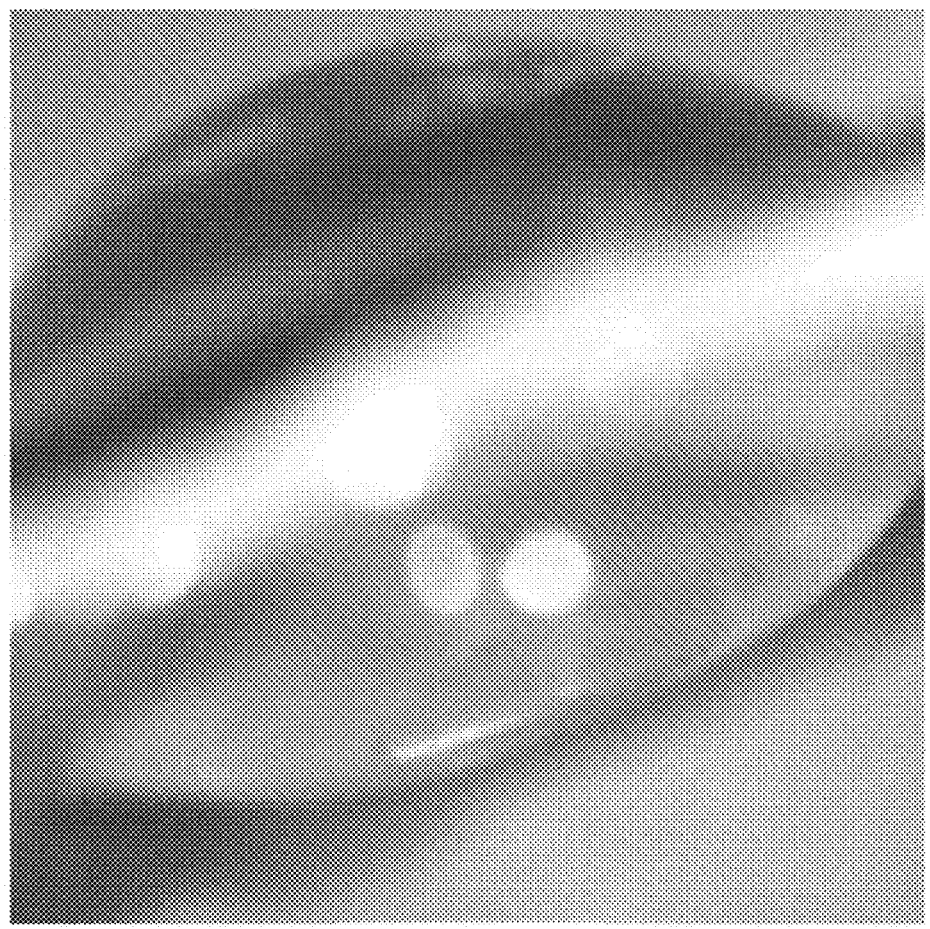
FIG. 18 is a side view of a second pig cadaver eye with a dual lens system.

Still another embodiment of the anterior lens 101 can be seen in FIG. 8. In this embodiment, a circular lens 801 similar to that shown in FIG. 4 is provided. In this embodiment, a small positioning cavity 802 is provided within the exterior of the lens. The positioning cavity 802 allows the surgeon to hold the IOL in place while the accommodation material is injected into the capsular bag. The positioning cavity can also be used to reposition the lens as needed after the accommodation material is in place. The cavity should be large enough to be used by a probe or a surgical instrument yet small enough not to interfere with the patient's vision after implantation. Typically the cavity will have a diameter of 0.3 mm or less. As shown in FIG. 9, the positioning cavity may be shaped such that the interior diameter of the cavity 901 is greater than the opening of the cavity 902 creating a lip 903, at the opening of the cavity. This allows the surgeon to engage the lip 903 of the cavity with a probe or similar device to hold the lens. Alternatively, the position cavity can be simply a straight edged pocket.

The lenses used in the practice of the invention may be standard IOLs or may be adjustable IOLs such as those described in U.S. Pat. No. 6,450,642.

The accommodation material comprises an injectable material that is firm enough to support the lenses of the system, but flexible enough to provide accommodation when placed in the capsular bag. The accommodation material binds to the walls of the capsular bag aiding the accommodation process. After the composition is placed in the capsular bag and, if necessary, crosslinked in vivo, it exhibits sufficient elastic properties such that as the muscles on either side of the capsular bag extend or contract, they cause the composition to extend or contract. This, in turn, shifts the position of the IOL forward or backward, thus providing accommodation with change of focus. In addition, the curvature of the filled capsular bag changes with the muscle movement during accommodation. The elastic and mechanical properties of the accommodation material can be adjusted, in vivo, through the use of macromers present in the composition, exposure to an external stimulus such as light.

In one embodiment, the accommodation material comprises a first and second component which, when cured in the eye, form a polymer matrix within the capsular bag between the anterior lens and posterior lens implanted in the eye. In yet another embodiment, dispersed within the matrix is a macromer or mixture of macromers capable of stimulus induced polymerization.

Once in place and if needed, cured, the accommodation material serves to assist in the accommodation process. As the zonules pull at the capsular bag, the shape of the bag changes. This in turn puts pressure on the polymer matrix causing the matrix to change shape and thereby shift the position of the IOL. The macromer, if present in the accommodation material, can be used to adjust the physical properties of the matrix making it more or less flexible. This in turn, affects that movement of the IOL when the capsular bag changes shape. Both the shape change of the capsular bag and the movement of the IOL as a result of the change of this composition provide the accommodation in present invention.

As discussed above, the accommodation material also may comprise macromers possessing functional groups. The physical properties of the cured accommodation material can be adopted by cross-linking the functionalized macromer. This is accomplished by exposing the functionalized macromers to an external stimulus such a light. In a preferred embodiment, the external stimulus is ultraviolet light.

The accommodation material used in the practice of the invention should exhibit an elastic modulus similar to that of the natural lens, typically between about 100 and about 1000 Pa. For example for a young human lens, an elastic modulus of from about 400 to about 600 Pa is preferred. This allows the accommodation material to deform and recoil when the muscles exert and release force on the zonules attached to the capsular bag. The accommodation material should initially also be of sufficiently low viscosity to allow injection into the capsular bag.

The accommodation material should also have optical properties that do not interfere with the function of the IOL. In general, this means that the refractive index of the material in the capsular bag should be similar to that of a lens or aqueous humor. Typically, this would be from about 1.33 to about 1.50. In one embodiment, the refraction index varies from about 1.41 to about 1.43.

The accommodation material may comprise a fully crosslinked polymer that can be directly injected into the capsular bag or it may comprise one or more precursors, which, when injected into the capsular bag, cure to form a crosslinked structure. The latter materials can include crosslinkable esters of hyaluronic acid, collagen, hydrogels of poly (N,N.-isopropylacrylamide and functional silicone compounds. Examples of collagen based materials useful in the practice of the invention include those disclosed in U.S. Pat. Nos. 5,476,515 and 5,910,537.

For the adjustable accommodation material, illustrative examples of a suitable first polymer matrix include: poly-acrylates such as poly-alkyl acrylates and poly-hydroxyalkyl acrylates; poly-methacrylates such as poly-methyl methacrylate ("PMMA"), poly-hydroxyethyl methacrylate ("PHEMA"), and poly-hydroxypropyl methacrylate ("PHPMA"); poly-vinyls such as poly-styrene and poly-N-vinylpyrrolidone ("PNVP"); poly-siloxanes such as poly-dimethylsiloxane, dimethylsiloxane diphenylsiloxane copolymers, dimethylsiloxane methylphenylsiloxane copolymers; poly-phosphazenes; urethanes and copolymers thereof. U.S. Pat. No. 4,260,725 and patents and references cited therein (which are all incorporated herein by reference) provide more specific examples of suitable polymers that may be used to form the first polymer matrix.

In preferred embodiments, the first polymer matrix of the accommodation material generally possesses a relatively low glass transition temperature ("$T_g$") such that the resulting IOL tends to exhibit fluid-like and/or elastomeric behavior, and is typically formed by crosslinking one or more polymeric starting material wherein each polymeric starting material includes at least one crosslinkable group. Illustrative examples of suitable crosslinkable groups include but are not limited to hydride, vinyl, acetoxy, alkoxy, amino, anhydride, aryloxy, carboxy, enoxy, epoxy, halide, isocyano, olefinic, and oxime. In more preferred embodiments, each polymeric starting material includes terminal monomers (also referred to as endcaps) that are either the same or different from the one or more monomers that comprise the polymeric starting material but include at least one crosslinkable group. Consequently, other embodiments include crosslinkers that have reactive groups attached as sidegroups along the backbone and/or terminal endcaps. In other words, the terminal monomers begin and end the polymeric starting material and include at least one crosslinkable group as part of its structure. Although it is not necessary for the practice of the present invention, the mechanism for crosslinking the polymeric starting material preferably is different than the mechanism for the stimulus-induced polymerization of the components that comprise the refraction modulating accommodation material. For example, if the refraction modulating accommodation material is polymerized by photo-induced polymerization, then it is preferred that the polymeric starting materials have crosslinkable groups that are polymerized by any mechanism other than photo-induced polymerization.

An especially preferred class of polymeric starting materials for the formation of the first polymer matrix is polysiloxanes (also know as "silicones") endcapped with a terminal monomer which includes a crosslinkable group selected from the group comprising acetoxy, amino, alkoxy, halide, hydroxy, vinyl, hydride and mercapto. Because silicone IOLs tend to be flexible and foldable, generally smaller incisions may be used during the IOL implantation procedure. An example of an especially preferred polymeric starting material is bis(diacetoxymethylsilyl)-polydimethylsiloxane (which is poly-dimethylsiloxane that is endcapped with a diacetoxymethylsilyl terminal monomer). Another example involves hydrosilylation reactions between the vinyl- and the hydride-functionalized silicones in presence of a catalyst, preferably a platinum complex and is similar to the accommodation materials described in the U.S. Pat. No. 5,411,553 and others.

In the present invention, the first polymer matrix is formed in vivo. This is accomplished in injecting the precursors for the first polymer matrix as well as the refraction- and/or shape-modifying accommodation material into a body cavity and allowing the precursors of the first polymer matrix to cure in the presence of the refraction- and/or shape-modifying accommodation material. The curing is accomplished through catalytic polymerization of the first and second precursor.

Where the first polymer matrix is a silicone-based matrix, two types of precursors are required to form the first polymer matrix useful in the practice of the invention. The first precursor comprises one or more vinyl-containing polyorganosiloxanes and the second precursors comprise one or more organosilicon compounds having silicon-bonded hydride groups which react with the vinyl groups of the first precursor.

The first precursor preferably has an average of at least two silicone-bonded vinyl groups per molecule. The number of vinyl groups can vary from two per molecule. For example the first precursor can be a blend of two or more polyorganosiloxanes in which some of the molecules have more than two vinyl groups per molecule and some have less than two vinyl groups per molecule. Although it is not required that the silicon-bonded vinyl groups be located in the alpha, omega (i.e. terminal) positions, it is preferred that at least some of the vinyl radicals be located at these positions. The vinyl groups are located at the polymer ends because such polyorganosiloxanes are economical to produce and provide satisfactory products. However, because of the polymeric nature of the first precursor, its preparation may result in products that have some variation in structure, and some vinyl groups may not be in the terminal position, even if the intent is to have them in these positions. Thus, the resulting polyorganosiloxanes may have a portion of the vinyl radicals located at branch sites.

The polyorganosiloxanes of the first precursor are preferably essentially linear polymers that may have some branching. The polyorganosiloxanes may have silicon-oxygen-silicon backbones with an average of greater than two organo groups per silicon atom. Preferably, the first precursor is made up of diorganosiloxane units with triorganosiloxane units for endgroups, but small amounts of monoorganosiloxane units and $SiO_2$ may also be present. The organo groups preferably have less than about 10 carbon atoms per group and are each independently selected from monovalent hydrocarbon groups such as methyl, ethyl, vinyl propyl, hexyl and phenyl and monovalent substituted hydrocarbon groups such as perfluoroalkylethyl groups. Examples of first precursors include dimethylvinylsiloxy endblocked polydimethylsiloxane, methylphenylvinylsiloxy endblocked polydimethylsiloxane, dimethylvinylsiloxy endblocked polymethyl-(3,3,3-triflouropropyl) siloxane, dimethylsiloxy endblocked polydiorganosiloxane copolymers of dimethylsiloxane units and methylphenylsiloxane units and methylphenylvinylsiloxy endblocked polydiorganosiloxane copolymers of dimethylsiloxane units and diphenylsiloxane units and the like. The polydiorganosiloxane can have siloxane units such as dimethylsiloxane units, methylphenylsiloxane units, methyl-(3,3,3-trifluoropropyl)siloxane units, monomethylsiloxane units, monophenylsiloxane units, dimethylvinylsiloxane units, trimethylsiloxane units, and $SiO_2$ units. Polyorganosiloxanes of the first precursor can be single polymers or mixtures of polymers. These polymers may have at least fifty percent of the organic groups as methyl groups. Many polyorganosiloxanes useful as the first precursor are known in the art and are commercially available. A preferred first precursor is polydimethylsiloxane endblocked with dimethylvinylsiloxy units or methylphenylsiloxy units having a viscosity of from about 500 to 100,000 centipoise at 25° C.

The second precursor includes organosilicon compounds containing at least 2, and preferably at least 3, silicon-bonded hydride groups, i.e., hydrogen atoms, per molecule. Each of the silicon-bonded hydride groups is preferably bonded to a different silicon atom. The remaining valences of the silicon atom are satisfied by divalent oxygen atoms or by monovalent groups, such as alkyl having from 1 to about 6 carbon atoms per group, for example methyl, ethyl, propyl, isopropyl, butyl, tertiary butyl, pentyl hexyl, cyclohexyl, substituted alkyl groups, aryl groups, substituted aryl groups and the like. The silicon-bonded hydride group containing organosilicon compounds can be homopolymers, copolymers and mixtures thereof which contain siloxane units of the following types: $RSiO_{1.5}$, $R_2SiO$, $RHSiO$, $HSiO_{1.5}$, $R_2HSiO_{0.5}$, $H_2SiO$ $RH_2SiO^{0.5}$, and $SiO$ where R is the monovalent group, for example, as defined above. Examples include polymethylhydrogensiloxane cyclics, copolymers of trimethylsiloxy and methylhydrogensiloxane, copolymers of dimethylsiloxy and methylhydrogensiloxane, copolymers of trimethylsiloxy, dimethylsiloxane and methylhydrogensiloxane, copolymers of dimethylhydrogensiloxane, dimethylsiloxane and methylhydrogensiloxane and the like. Also needed is a crosslinker resin. This resin is a multifunctional vinyl silicone of certain molecular weight, branched structure and functionality. The other crosslinker is the multifunctional silicone hydride of certain molecular weight, branched structure and functionality.

The platinum group metal catalyst component can be any of the compatible platinum group metal-containing catalysis known to catalyze the addition of silicone-bonded hydrogen atoms (hydride groups) to silicon-bonded vinyl radicals. Platinum group metal-containing catalysts can be any of the known forms which are compatible, such as platinic chloride, salts of platinum, chloroplatinic acid and various complexes. The platinum group metal-containing catalyst can be used in any catalytic quantity, such as in an amount sufficient to provide at least about 0.1 ppm weight of platinum group metal (calculated as elemental metal) based on the combined weight of the first and second precursors. Preferably, at least 10 ppm, or more preferably, at least about 20-40 ppm by weight of platinum group metal based on the combined weight of the first and second precursors is used.

The first component further comprises a catalyst to induce the polymerization of the first and second components to form the polymer matrix in the capsular bag.

The accommodation material of the invention may also comprise a accommodation material modifier or macromer which is capable of modifying the characteristics of the accommodation material in vivo. In the preferred embodiment, the macomers are capable of modifying the elastomer properties of this polymer matrix. This is accomplished by stimulus induced polymerization of the macromer, which is further accomplished through the use of functional groups on the macromers that are capable of stimulus induced polymerization. Upon exposure to the appropriate external stimulus, e.g. heat or light, the macromer polymerizes to form a second polymer matrix. This polymerization causes changes in the properties of the crosslinked accommodation material. The external stimulus is generally provided by an external energy source.

The modifying accommodation material that is used in practice of the invention is as described above except that it has the preferred requirement of biocompatibility. The refraction- and/or shape-modifying accommodation material is capable of stimulus-induced polymerization and may be a single component or multiple components so long as: (i) it is compatible with the formation of the first polymer matrix; (ii) it remains capable of stimulus-induced polymerization after the formation of the first polymer matrix; (iii) it is freely diffusible within the first polymer matrix. In general, the same type of monomer that is used to form the first polymer matrix may be used as a component of the shape-modifying accommodation material. The monomers will often contain functional groups that are capable of stimulus-induced polymerization. However, because of the requirement that the modifying monomers must be diffusable within the first polymer matrix, the modifying monomers generally tend to be smaller (i.e., have lower molecular weights) than the first polymer matrix network, i.e., the diffusible materials have to be of molecular weight less than for instance the molecular weight between crosslinks of the first polymer matrix. In addition to the one or more monomers, the accommodation material may include other components such as initiators and sensitizers that facilitate the formation of the second polymer matrix. In addition, to provide the UV-blocking properties similar to the natural eye, UV-absorbers may also be incorporated as a component of the refraction- and/or shape-modifying accommodation material.

In some embodiments, the stimulus-induced polymerization is photopolymerization. In other words, for the one or more monomers that comprise the refraction- and/or shape modulating accommodation material, each preferably includes at least one functional group that is capable of photopolymerization. Illustrative examples of such photopolymerizable groups include but are not limited to acrylate, allyloxy, cinnamoyl, methacrylate, stibenyl, and vinyl. In more preferred embodiments, the refraction- and/or shape-modifying accommodation material includes a photoinitiator (any compound used to generate free radicals) either alone or in the presence of a sensitizer and UV-absorbers. Examples of suitable photoinitiators include acetophenones (e.g., substituted haloacetophenone, and diethoxyacetophenone); 2,4-dichloromethyl-1,3,5-triazines; benzoin methyl ether; and o-benzoyl oximino ketone and silicone derivatives thereof. Examples of suitable sensitizers include p-(dialkylamino)aryl aldehyde; N-alkylindolylidene; and bis[p-(dialkylamino)benzylidene]ketone and silicone derivatives thereof. Examples of UV-absorbers include but are not limited to the benzophenones and their derivatives, benzotriazoles and their derivatives, and others that are known in the art of UV-blocking materials.

One class of macromers useful in the practice of the invention includes poly-siloxanes endcapped with a terminal siloxane moiety that includes a photopolymerizable group. An illustrative representation of such a monomer is:

wherein Y is a siloxane which may be a monomer, a homopolymer or a copolymer formed from any number of siloxane units, and X and X1 may be the same or different and are each independently a terminal siloxane moiety that includes a photopolymerizable group. An illustrative example of Y includes:

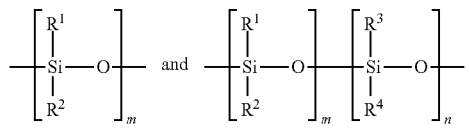

wherein: m and n are independently each an integer and $R^1$, $R^2$, $R^3$, and $R^4$ are independently each hydrogen, alkyl (primary, secondary, tertiary, cyclo), aryl, or heteroaryl. In preferred embodiments, $R^1$, $R^2$, $R^3$, and $R^4$ are $C_1$-$C_{10}$ alkyl or phenyl. Because shape-modifying accommodation material monomers with a relatively high aryl content have been found to produce larger changes in the refractive index of the inventive lens, it is generally preferred that a least one of $R^1$, $R^2$, $R^3$, and $R^4$ is an aryl, particularly phenyl. In more preferred embodiments, $R^1$, $R^2$, and $R^3$ are the same and are methyl, ethyl or propyl and $R^4$ is phenyl.

Illustrative examples of X and X1 (or X1 and X depending on how the RSMC polymer is depicted) are

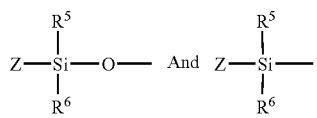

respectively wherein:

$R^5$ and $R^6$ are independently each hydrogen, alkyl, aryl, or heteroaryl; and Z is a photopolymerizable group.

In preferred embodiments, $R^5$ and $R^6$ are independently each a $C_1$-$C_{10}$ alkyl or phenyl and Z is a photopolymerizable group that includes a moiety selected from the group consisting of acrylate, allyloxy, cinnamoyl, methacrylate, stibenyl, and vinyl. In more preferred embodiments, $R^5$ and $R^6$ is methyl, ethyl, or propyl and Z is a photopolymerizable group that includes an acrylate or methacrylate moiety.

In especially preferred embodiments, the refraction- and/or shape-modifying accommodation material monomer is of the following formula:

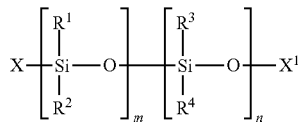

wherein X and $X^1$ are the same and $R^1$, $R^2$, $R^3$, and $R^4$ are as defined previously. Illustrative examples of such shape-modifying accommodation material monomers include dimethylsiloxane-diphenylsiloxane copolymer endcapped with a vinyl dimethylsilane group; dimethylsiloxane-methylphenylsiloxane copolymer endcapped with a methacryloxypropyl dimethylsilane group; and dimethylsiloxane endcapped with a methacryloxypropyldimethylsilane group. Although any suitable method may be used, a ring-opening reaction of one or more cyclic siloxanes in the presence of triflic acid has been found to be a particularly efficient method of making one class of inventive shape-modifying accommodation material monomers. Briefly, the method comprises contacting a cyclic siloxane with a compound of the formula:

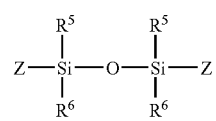

in the presence of triflic acid wherein $R^5$, $R^6$, and Z are as defined previously. The cyclic siloxane may be a cyclic siloxane monomer, homopolymer, or copolymer. Alternatively, more than one cyclic siloxane may be used. For example, a cyclic dimethylsiloxane tetramer and a cyclic methyl-phenylsiloxane trimer/tetramer are contacted with bis-methacryloxypropyltetramethyldisiloxane in the presence of triflic acid to form a dimethylsiloxane methylphenylsiloxane copolymer that is endcapped with a methacryloxypropyldimethylsilane group, an especially preferred shape-modifying accommodation material monomer. The accommodation material also may crosslink these.

The IOLs that may be used in the practice of the invention include all types of prefabricated IOLs including single lens IOL, adjustable IOLs, multi lens IOLs, and accommodating IOLs such as those described in U.S. Pat. No. 5,275,623. In the case of the latter both type of lenses, the accommodation material of the invention may be used to fill the space between the different lenses as well as any space between the lens and the capsular bag.

In practice of the invention, the existing lens is removed from the patient's eye by any standard procedure, preferably phacoemulsification. The posterior and anterior lenses then implanted, using standard surgical procedures. Once the lenses are properly positioned, the accommodation material of the invention is then introduced into the capsular bag in the space between the anterior and posterior lenses through the injection hole of the anterior lens.

In the case where a multiple component system is used to form the accommodation material, the different components are kept separate until the materials are implanted in the bag with curing taking place in vivo. This is best accomplished with a multichamber syringe such that the components are combined just before the accommodation material is injected into the capsular bag. The capsular bag is filled with the accommodation material of the invention while the material is curing. The anterior lens acts as a plug to hold the accommodation material in place in the manner described above.

In the practice of the invention, the natural lens is removed by phaco-emulsification leaving the lens capsule intact with a capsulorhexis of 4-6 mm in diameter. The monomers or polymer precursors necessary to form the first polymer matrix as well as the refraction or shape-modifying accommodation material are mixed, precured, if appropriate, and injected into the body cavity such that the first polymer matrix is formed in the body cavity. Alternately, the first polymer precursor and the refraction- and/or shape modifying accommodation material are mixed, degassed, transferred to a syringe, and cooled to a temperature (between −10° to 0° C.) at which the first polymer matrix crosslinking is inhibited. The shape-modifying accommodation material monomers as well as any initiators required to form the second polymer matrix and other components, such as UV absorber, are mixed with the first polymer matrix monomers before injection into the body cavity. In another embodiment, a small tube is used to direct the accommodation material through an opening in the edge of the anterior lens or in the haptic holding the anterior lens in place.

Prior to the implantation of the accommodation material into the capsular bag, it may be necessary to irrigate the bag to reduce the possibility of posterior capsular opacification ("PCO"). Proper sealing of the capsular bag may also prevent PCO. Methods for accomplishing irrigation and sealing of the capsular bag are known in the art. For example, plugs may be used to seal the bag.

For the accommodation material of the invention, the curing temperature for the first polymer matrix is the physiological temperature of the eye, for example, in humans in the range of about 35° C. to about 37° C. Lack of mobility of the injected accommodation material preferably occurs about 20 minutes after injection, more preferably within about 10 minutes. Final cure preferably occurs within about 6 hours, more preferably within about 2 hours of injection.

In one embodiment of the invention, the first and second precursors are separated into two discrete precursor mixtures. The first precursor mixture comprises the first accommodation material precursor combined with the refraction- and/or shape-modifying material (macromer), photoinitiator and, where desired, an UV-absorber. In the second precursor mixture, the second accommodation material precursor and catalyst are combined. Alternatively, the catalyst can be combined with the first precursor and the other components combined with the second precursor. In these embodiments, the first and second precursors and the catalyst are kept separate until just before the materials are injected into the body cavity.

A preferred way to prepare the accommodation material of the present invention is through use of a multichamber syringe which keeps the individual components separate until just before the components are injected into the body cavity. The individual components may be sterilized with steam or by other sterilization methods compatible with the individual components. While each component may be injected separately, some components may be combined provided that they do not interact such that they fail to perform as required once they are injected into the body cavity. For example, where the first polymer matrix is formed from two separate monomers in the presence of a catalyst, one chamber of the syringe will contain the first monomer and the second chamber will contain the other monomer. The catalyst can be combined with either monomer unless the catalyst will cause the monomer to polymerize in the chamber. Additional components can be combined in one of the other chambers. For example, the refraction- and/or shape-modifying components can be placed in either chamber as well as any other additives. In the case of intraocular lenses, the additives can include UV absorber such as benzotriazoles, benzophenones, phenylesters, cinnamic acid and derivatives and nickel-containing compounds. The additions may also include stimulus induced initiators for crosslinking the macromers in vivo. These are typically photoinitiators with UV based photoinitiators preferred.

In one embodiment, the accommodation material is injected directly into the capsular bag through the wall of the bag. In another embodiment, the accommodation material passes through injection ports in the outer edge of the outlined anterior IOL as described above. In one embodiment, a flexible tube is used to connect the syringe to the injection port.

An advantage of the present invention is that properties of the accommodation material may be modified after implantation within the body. For example, the flexural modulus of the accommodation material may be modified in a post-surgical outpatient procedure.

In addition to the change in the elastomeric properties of the accommodation material, the shape of the resulting polymer matrix can be adjusted. As a result, both mechanisms may be exploited to provide accommodation. In general, the process for modifying the accommodation material of the invention comprises:

(a) exposing at least a portion of the accommodation material to an external stimulus whereby the stimulus induces the polymerization of the modifying accommodation material. If after formation of the accommodation material and wound healing, no accommodation material property needs to be modified, then the exposed portion is the entire implant. The exposure of the entire accommodation material will lock in the then-existing properties of the implanted implant. However, if an implant characteristic such as the power of an IOL needs to be modified, then only a portion of the implant (something less than the entire implant) would be exposed. In one embodiment, the method of implementing the inventive implant further comprises:

(b) waiting an interval of time; and (c) re-exposing the portion of the implant to the stimulus.

This procedure generally will induce the further polymerization of the refraction modulating accommodation material within the exposed implant portion. Steps (b) and (c) may be repeated any number of times until the implant has reached the desired implant characteristic. At this point, the method may further include the step of exposing the entire implant to the stimulus to lock-in the desired lens property.

In another embodiment where an adjustable anterior lens is employed and a lens property needs to be modified, the method for implementing an inventive IOL system comprises:

(a) exposing a first portion of the anterior lens to a stimulus whereby the stimulus induces the polymerization of the refraction modulating accommodation material; and (b) exposing a second portion of the lens to the stimulus.

The first lens portion and the second lens portion represent different regions of the lens although they may overlap. Optionally, the method may include an interval of time between the exposures of the first lens portion and the second lens portion. In addition, the method may further comprise re-exposing the first lens portion and/or the second lens portion any number of times (with or without an interval of time between exposures) or may further comprise exposing additional portions of the lens (e.g., a third lens portion, a fourth lens portion, etc.). Once the desired property has been reached, then the method may further include the step of exposing the entire lens to the stimulus to lock-in the desired lens property.

In a third embodiment, the properties of both the adjustable lens and the accommodation material can be manipulated in the manner described above.

EXAMPLES

Example 1

A series of four experiments were conducted by first removing the natural lens of a rabbit by phaeco-emulsification.

In two of the experiments, a dual lens intraocular lens system was implanted and in the other two, a single lens system was implanted. The capsular bag was then filled with a composition comprising a soft silicone gel mixture with a refractive index of 1.41. The silicone mixture was cured in the eye within an hour.

After 17 days, the eyes were examined. The capsular bag remained well filled with no signs of leakage. As shown in FIGS. 10-13, the posterior lens or posterior of the capsule was clearly visible in each case.

Example 2

A series of experiments were conducted using pig cadaver eyes. The pig eye was fixtured on a stand and the natural lens was removed by phaeco-emulsification. A 3-piece silicone IOL was implanted behind the capsulorhexis opening. The capsular bag was then filled with a hydrogel composition comprising of copoly(2-hydroxyethyl methacrylate and N,N-dimethyl acrylamide) behind the implanted IOL. The eye was well filled without any leakage.

Example 3

A series of experiments were conducted using pig cadaver eyes. The pig eye was fixtured on a stand and the natural lens was removed by phaeco-emulsification. A 3-piece commercial available soft acrylic IOL was implanted behind the capsulorhexis opening. The capsular bag was then filled with a composition comprising of soft silicone gel mixture behind the implanted IOL. The eye was well filled without any leakage. The IOL was able to provide the seal to the injectable material.

Example 4

A series of experiments were conducted using pig cadaver eyes. The pig eye was fixtured on a stand and the natural eye was removed by phaco-emulsification. A dual lens intraocular lens system consisting of a posterior 3-piece silicone IOL and either a soft acrylic or silicone disc plate anterior lens with an injection port was implanted. The capsular bag was then filled with a composition comprising of soft silicone gel mixture of refractive index of 1.41. The silicone gel was cured at room temperature for a few hours.

Figure 19:
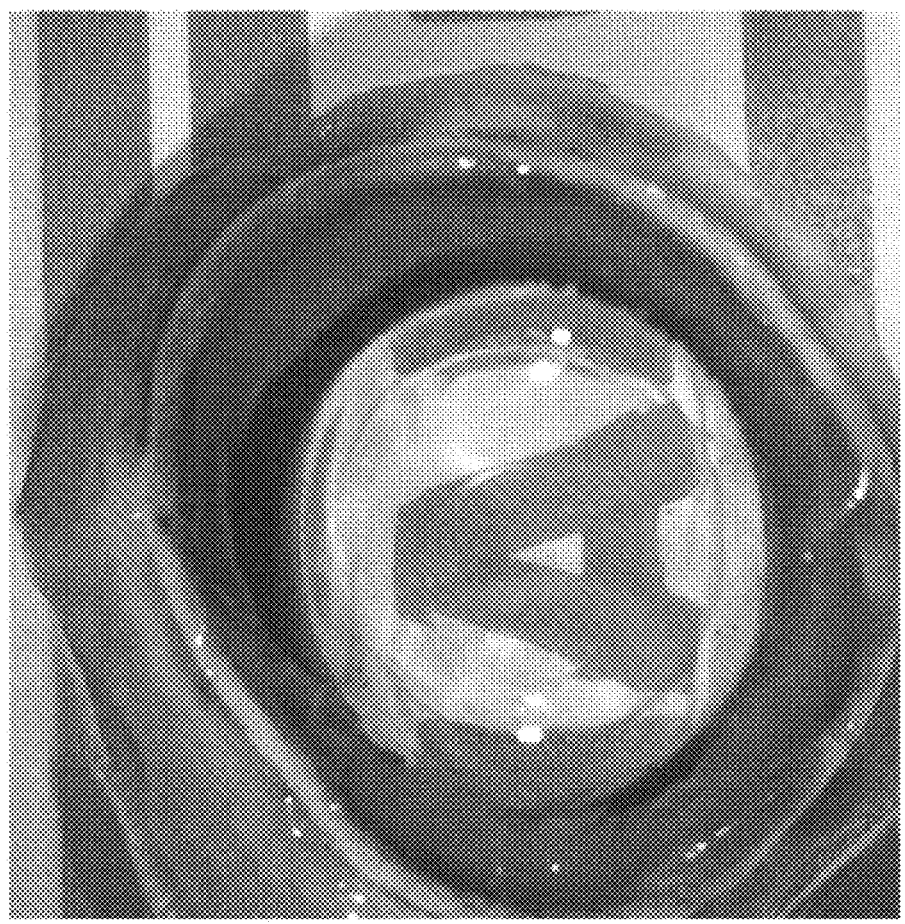
FIG. 19 is a posterior view of a pig cadaver eye with a dual lens system.

As shown in FIGS. 14-19, the capsular bag remained well filled with no sign of leakage as shown in FIG. 19. Clear images were projected from the filled pig eyes. The anterior IOL was able to provide the seal to the injectable material. Additionally, the dual lens intraocular system demonstrated to be an excellent optic.

Example 5

This example was conducted in the same manner as Example 4 above except that a light adjustable anterior accommodative IOL was implanted. The results were similar to that achieved in Example 4.

Example 6

The experiment was similar to Example 4 except that a light adjustable silicone gel injectable material was used in the accommodation material. Again, the results were similar to those observed in Example 4.

Example 7

This example was similar to Example 4 except that a light adjustable anterior accommodation IOL was implanted in the eye and the accommodation material was a light adjustable implantable silicon gel. Again, the result observed was similar to those in Example 4.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of the ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An intraocular lens system comprising:
   an anterior lens;
   a posterior lens;
   an accommodation material capable of use within a capsular bag and capable of being placed between said anterior and posterior lenses,
   wherein said anterior and posterior lenses have different optical properties to provide different degrees and types of correction,
   wherein said anterior lens has a positive diopter power,
   wherein said posterior lens has a negative diopter power,
   wherein the accommodation material is capable of changing shape, and this change in shape facilitates the movement of the posterior lens and the anterior lens in response to the capsular bag extending or contracting with a change of focus of the intraocular lens system,
   wherein said accommodation material comprises macromers dispersed therein, said macromers capable of stimulus induced polymerization to adjust physical properties of the matrix making it more or less flexible for responding to extension or contraction in the capsular bag with the change of focus, and
   wherein said anterior lens has a plate haptic surrounding said anterior lens and having from 2 to 4 haptic arms.

2. The intraocular lens system of claim 1 wherein the accommodation material is formed in vivo.

3. The intraocular lens system of claim 2 wherein the macromers are capable of photopolymerization.

4. The intraocular lens of claim 1 wherein the anterior lens is adjustable.

5. The intraocular lens system of claim 1 wherein said anterior lens comprises an injection port.

6. The intraocular lens of claim 1 wherein said anterior lens comprises a positioning cavity.

7. The intraocular lens of claim 1 wherein the edges of the posterior lens are squared.

8. The intraocular lens system of claim 1 wherein said accommodation material has an elastic modulus of from about 100 to about 1000 Pa.

9. The intraocular lens of claim 1 wherein the accommodation material has a refraction index of from about 1.33 to about 1.50.

10. The intraocular lens of claim 1 wherein the accommodation material comprises a polymer selected from the group consisting of polyacrylates, polyvinyls, polysiloxanes, polyphosphazenes, urethanes and copolymers thereof.

11. An intraocular lens system comprising:
an anterior lens;
a posterior lens;
an accommodation material capable of use within a capsular bag and capable of being placed between said anterior lens and said posterior lens wherein said anterior lens comprises an adjustable lens,
wherein said anterior and posterior lenses have different optical properties to provide different degrees and types of correction,
wherein said anterior lens has a positive diopter power,
wherein said posterior lens has a negative diopter power,
wherein the accommodation material is capable of changing shape, and this change in shape facilitates the movement of the posterior lens and the anterior lens in response to the capsular bag extending or contracting with a change of focus of the intraocular lens system,
wherein the accommodation material comprises macromers dispersed therein, said macromers capable of stimulus induced polymerization to adjust physical properties of the matrix making it more or less flexible for responding to extension or contraction in the capsular bag with the change of focus, and
wherein said anterior lens has a plate haptic surrounding said anterior lens and having from 2 to 4 haptic arms.

12. The intraocular lens system of claim 11 wherein the accommodation material is formed in vivo.

13. The intraocular lens system of claim 11 wherein said macromers are capable of photopolymerization.

14. The intraocular lens system of claim 11 wherein said anterior lens comprises an injection port.

15. The intraocular lens system of claim 11 wherein the edges of said posterior lens are squared.

16. The intraocular lens of claim 11 wherein said accommodation material has an elastic modulus of from about 100 to about 1000 Pa.

* * * * *